United States Patent

Wood

[11] Patent Number: 5,887,745
[45] Date of Patent: Mar. 30, 1999

[54] STERILIZATION AND STORAGE CONTAINER LATCH

[75] Inventor: Timothy E. Wood, Weare, N.H.

[73] Assignee: Poly Vac, Inc., Manchester, N.H.

[21] Appl. No.: 976,157

[22] Filed: Nov. 21, 1997

[51] Int. Cl.$^6$ ................................................ B65D 43/08
[52] U.S. Cl. ......................... 220/326; 229/145; 229/150
[58] Field of Search ..................... 220/324, 326, 220/622; 229/145, 146, 150

[56] References Cited

U.S. PATENT DOCUMENTS

| | | |
|---|---|---|
| 1,519,614 | 12/1924 | Heck . |
| 2,744,778 | 5/1956 | Cooke . |
| 2,893,771 | 7/1959 | Claud-Mantle . |
| 4,512,498 | 4/1985 | Leibinger . |
| 4,643,303 | 2/1987 | Arp et al. . |
| 4,728,504 | 3/1988 | Nichols . |
| 4,783,321 | 11/1988 | Spence . |
| 4,798,292 | 1/1989 | Hauze . |
| 4,817,799 | 4/1989 | Gregerson et al. ...................... 206/445 |
| 4,915,913 | 4/1990 | Williams et al. . |
| 4,959,199 | 9/1990 | Brewer . |
| 5,004,103 | 4/1991 | Connors et al. . |
| 5,065,885 | 11/1991 | Scaroni .................................. 220/326 |
| 5,098,676 | 3/1992 | Brooks, Jr. . |
| 5,174,453 | 12/1992 | Stoeffler . |
| 5,211,915 | 5/1993 | Mönch . |
| 5,232,116 | 8/1993 | Baxter ................................... 220/324 |
| 5,281,400 | 1/1994 | Berry, Jr. . |
| 5,353,930 | 10/1994 | Berry, Jr. . |
| 5,358,112 | 10/1994 | Gardner . |
| 5,368,161 | 11/1994 | Plais . |
| 5,384,103 | 1/1995 | Miller . |
| 5,415,846 | 5/1995 | Berry, Jr. . |
| 5,441,709 | 8/1995 | Berry, Jr. . |
| 5,490,975 | 2/1996 | Dane . |
| 5,518,115 | 5/1996 | Latulippe . |
| 5,525,314 | 6/1996 | Hurson . |
| 5,630,507 | 5/1997 | Baker . |
| 5,706,968 | 1/1998 | Riley . |

FOREIGN PATENT DOCUMENTS

| | | |
|---|---|---|
| 1364546 | 1/1988 | U.S.S.R. . |
| 2198119 | 6/1988 | United Kingdom . |
| WO96/22113 | 7/1996 | WIPO . |

OTHER PUBLICATIONS

Opti Care –Durable Scope Containers –1 p..
Poly Vac, Inc. –Date unknown.
Poly Vac, Inc. –Blending Form and Function –4 pp..
Poly Vac, Inc. –1996 –Connections Network, Inc.

*Primary Examiner*—Stephen K. Cronin
*Attorney, Agent, or Firm*—Hayes, Soloway, Hennessey, Grossman & Hage, P.C.

[57] ABSTRACT

A slide-latch for use on a container having a storage tray and a closing lid. The latch comprises a generally J-shaped body terminating in a hook portion, and having an elongate ovoid slot running therethrough. The latch is mounted to said lid on an elongate rod located within the slot. The rod in turn is mounted to said lid. The latch is slidably operable between a closed position wherein the hook portion secures the lid to the storage tray, and an open position wherein the lid is separable from the storage tray. A cam surface between the underside of the latch and the top surface of the lid locks the latch in a closed position.

10 Claims, 3 Drawing Sheets

STERILIZATION AND STORAGE CONTAINER LATCH

FIELD OF THE INVENTION

This invention relates generally to latches for cases and containers where the lid member is secured to a tray portion by means of one or more latches. The invention has particular utility when used in connection with sterilization, storage and transport container systems, for example, for medical surgical instruments, and the like, and will be described in connection with such utility, although other utilities are contemplated.

At the present time there are a variety of cases which are used for the sterilization, storage and transport of equipment, instruments and supplies and which include a tray portion and a closing lid member. While the lid member may be hinged along one edge to the tray portion, the lid member may also be separate and not attached to the tray portion. Regardless of the specific lid configuration, at least one side of the lid member must lift or pivot away from the tray portion in order for the end user to gain access to the interior storage area of the tray portion. Accordingly, it is desired to be able to secure this one side in a closed condition against a corresponding side or edge of the tray portion. When the lid is completely separate from the tray portion, one or two pairs of latches, oppositely disposed, are normally used to secure the lid to the tray portion. A common means of securing the lid member and tray portion together is to use a multi-component latch with a double-action operating linkage. Typically one portion of the latch is anchored to the outer wall of the tray portion and a cooperating clamp portion of the latch extends up and over the outer peripheral edge of the lid member. Through the arrangement and interaction of various linkage members, the clamp portion is able to assume a free state so that it can be oriented over the edge of the lid member and then moved into a locked orientation.

One example of what has been only generally described is provided by U.S. Pat. No. 4,915,913. Another example is provided by U.S. Pat. No. 2,893,771. See also U.S. Pat. No. 2,744,778.

When a latch is being designed for a medical case, there are certain considerations which need to be factored into the latch configuration. Some of these considerations include the aesthetics of the design, the size, acceptable materials, and the absence of sharp corners or edges. Other considerations should include the specific method of use, the relative ease or difficulty in opening and closing the medical case, how secure is the latch, and whether there are any loose or free moving component parts.

While different customers and end users may prioritize these various considerations differently, the method of use and the relative ease or difficulty in manipulating the latch are believed to be near the top of every list. When the latch is to be used for a medical case, it is important to have a latch which is free of sharp corners or edges which might cut or puncture surgical gloves. If dangling or freely moving component parts can be avoided, there will be less noise and less risk of something catching on the component part. In turn, this then reduces the risk of the case being jarred or spilled. While it is important to have a secure clamping action of the lid member onto the tray portion, it is equally important to be able to easily release the latch.

The foregoing discussion of the prior art is taken largely from U.S. Pat. No. 5,630,507, in which there is described a latch for use on a container having a storage tray and closing lid and comprising a latch base having a mounting surface and means for attaching the latch base to the storage tray, a hook portion pivotally attached to the latch base, a release/closing lever pivotally attached to the latch and a pair of oppositely-disposed connecting links wherein each connecting link is connected at one end to the hook portion and at an opposite end to the lever such that the latch is operable between a closed condition wherein the hook portion secures tile closing lid to the storage tray and an open condition wherein the lid may be separated from the storage tray, the lever being pivotally movable so as to transition the latch from the closed condition to the open condition and back to the closed condition.

The present invention provides an improvement over latches such as described in accordance with the aforesaid prior art.

SUMMARY OF THE INVENTION

The present invention provides a single-action latch for use on a container having a storage tray and closing lid in which the latch comprises a generally J-shaped clasp formed of metal or plastic, and slidably mounted to the lid on a pin which in turn is affixed to risers or bosses formed on the lid. A cam surface located between the underside of the latch and the top of the lid, serves to selectively lock the latch between an open or unlocked position, and a closed or locked position.

BRIEF DESCRIPTION OF THE DRAWINGS

The foregoing and other objects of the present invention and various features and details of the operation and construction thereof will hereinafter be more fully set forth with reference to the accompanying drawings wherein like numerals depict like parts, and wherein.

DETAILED DESCRIPTION OF THE PREFERRED EMBODIMENT

Figure 1:
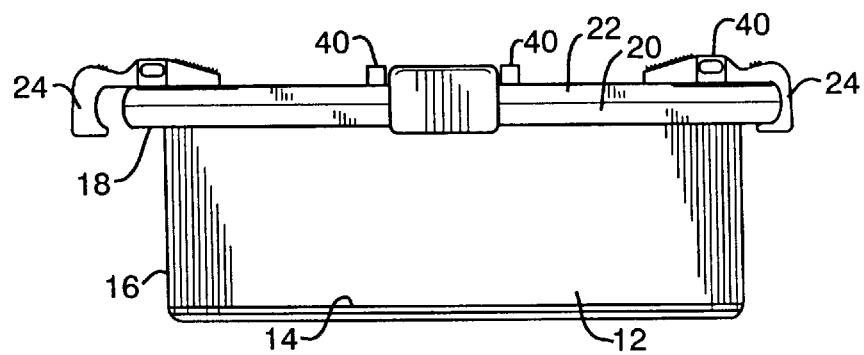
FIG. 1 is a side elevational view of a medical case including pairs of oppositely disposed latches according to a typical embodiment of the present invention.
Figure 2:
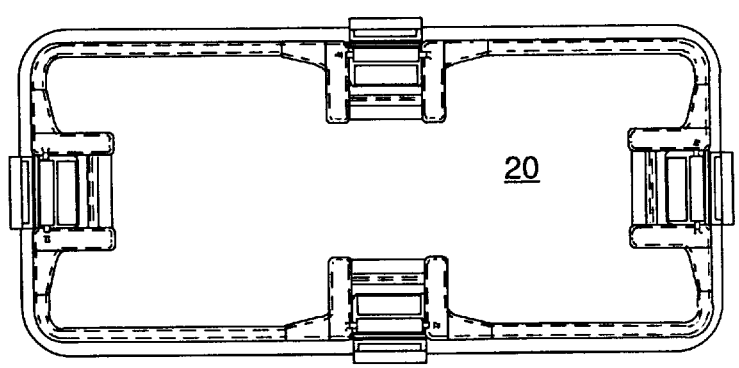
FIG. 2 is a top plan view of the FIG. 1 medical case.
Figure 3:
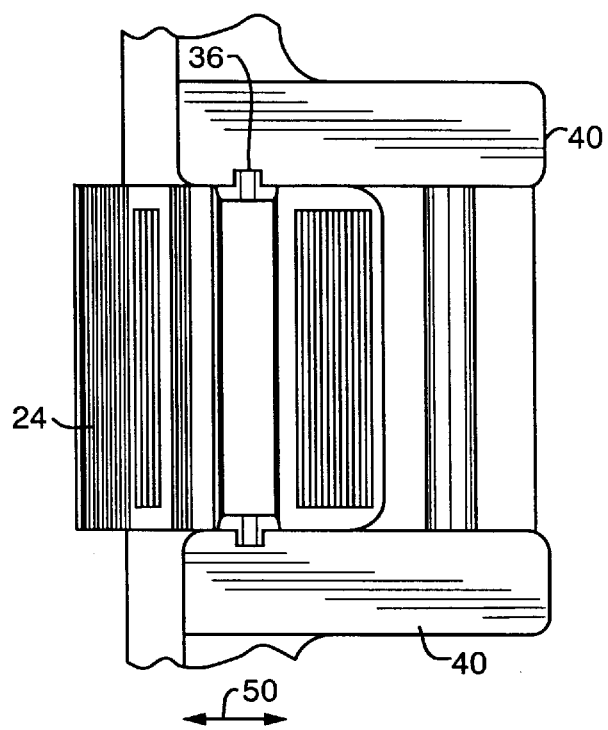
FIG. 3 is an enlarged top plan view of the portion designated "FIG. 3" in FIG. 2, and showing certain details of the sliding latch made in accordance with the present invention.
Figure 4:
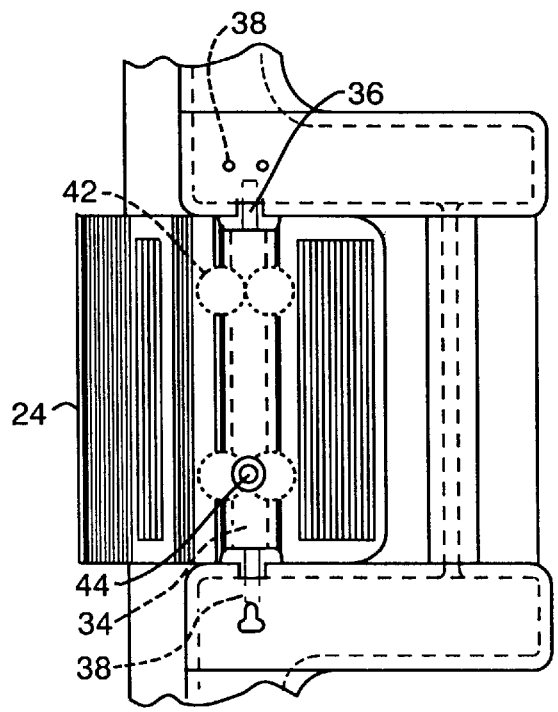
FIG. 4 is a view, similar to FIG. 3, and partially in phantom.
Figure 5:
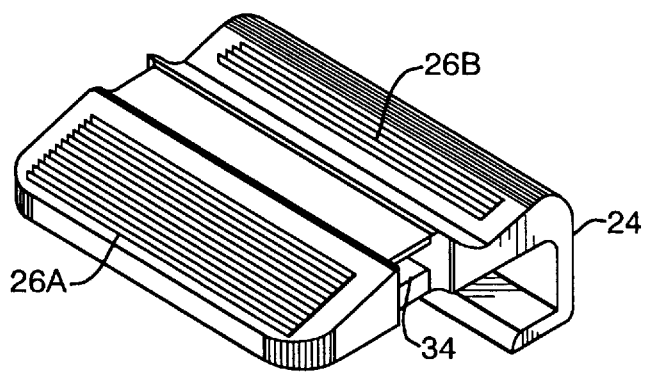
FIG. 5 is a perspective view of the latch element of the present invention.
Figure 6:
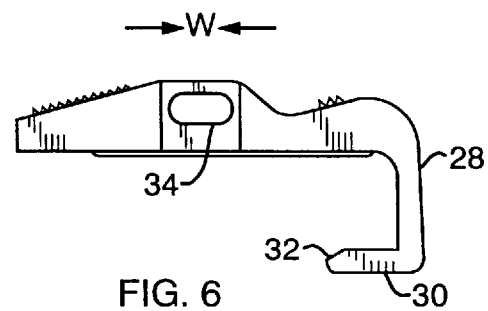
FIG. 6 is a side elevational view of the latch element shown in FIG. 5.
Figure 7:
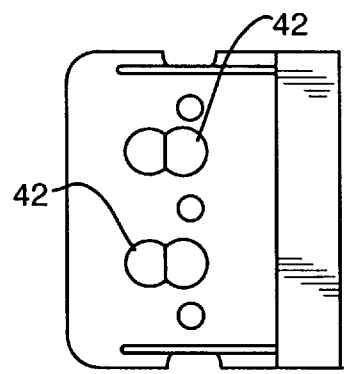
FIG. 7 is a bottom side view of the latch element portion of the present invention.

Referring now to the drawings, a sterilization, transporting and storage tray assembly of the present invention is indicated generally by numeral 10. The tray assembly 10 consists of a box-like bottom tray 12 having a bottom 14 and four generally perpendicular upwardly projecting continuous side walls 16 terminating in a flared lip 18. A lid or top 20 is fitted to the top of base 12. Lid 20 has a downwardly directed peripheral edge or lip 22 which is sized to have a close-fitting relationship around and over the peripheral lip 18 of base 12.

The base and lid include a plurality of holes or apertures (not shown) for permitting steam or other gaseous sterilants to ingress and egress the tray assembly 10. The tray assembly also includes one or more internal fixtures, mounting, racks and/or mats (also not shown) for holding surgical tools or other devices therein.

A feature and advantage of the present invention is to provide a single-action latch assembly which is secure, yet readily operable between a closed, locked position, and an open, unlocked position, and which may be operated using a single finger or thumb. Each latch 24 comprises a generally J-shaped member, formed of a resiliently flexible material, preferably plastic. Metal also may be used. Latch 24 comprises an elongate top wall having a top surface comprising serrated gripping surfaces 26A, 26B, and a perpendicularly directed side wall or web 28 terminating in a short inwardly directed wall 30 which runs essentially parallel to the top wall. Preferably, the distal edge of wall 30 is beveled at 32 to facilitate opening and closing of the latch over the bottom tray flared lip 18.

An elongate ovoid shaped slot 34 is formed through the top wall of latch 24, for accommodating a metal pin or rod 36. Pin 36 in turn is press-fitted into slots 38 formed in the underside of bosses 40 which in turn are formed on the top of lid 20.

One or more cam surfaces or nodes 42 are formed in the underside wall of latch 24 for interacting with a detent washer or bump 44 formed in or carried on the top surface of lid 20. Alternatively, cam surfaces may be formed on lid 20 with detent or bump formed or mounted on the bottom wall of latch 24.

Slot 34 has a width W which is significantly greater than the diameter of pin 36. As a result, latch 24 is slidably mounted, and may be moved back and forth, i.e. in the direction of arrows 50. As a result, latch 24 may be slid between a closed position, i.e. wherein the lower edge wall 30 engages the lip 18, i.e. as shown on the right-hand side of FIG. 1, and an open position wherein wall 30 clears lip 18 as illustrated in the position of the clamp in the left-hand side of FIG. 1.

The cam surface in the interface between the bottom of latch 24 and the top surface of lid 20 represents an "over-the-center" type of arrangement. As a result, when the lever 24 is pushed closed, the lid flexes away from the clamp sufficiently to clear the high point of the cam, causing the lever to lock in one node. Similarly, sliding the latch to an open position, the lid flexes away from the clamp whereby the clamp then locks in the open position in the other node.

The present invention provides a simple, single-action latch which may readily be opened and/or closed using a single finger or thumb. The latch also has smooth contours and thus is not likely to snag or rip surgical gloves or the like. Typically, latches are provided at opposite ends of the medical case so that they may simultaneously be opened and closed, contributing to convenience.

While the invention has been illustrated and described in connection with a preferred embodiment of the invention, it is understood that only the preferred embodiment has been shown and described, and that changes and modifications may be made in the foregoing invention without departing from the spirit and scope thereof.

I claim:

1. A slide-latch for use on a container having a storage tray and a closing lid, said latch comprising a generally J-shaped body terminating in a hook portion, and having an elongate ovoid slot running therethrough, said latch being mounted to said lid on an elongate rod located within said slot, said rod being mounted to said lid, whereby said latch is slidably operable between a closed position wherein said hook portion secures said lid to said storage tray, and an open position wherein said lid is separable from said storage tray, and a cam surface between the underside of said latch and the top surface of said lid for locking said latch in a closed position.

2. A latch according to claim 1, wherein said cam surface includes a node in which the latch is locked in an open position, and a node in which the latch is locked in a closed position.

3. A latch according to claim 1, wherein said cam surface is formed on the bottom of said latch.

4. A latch according to claim 3, wherein the cam surface is located on the top surface of said lid.

5. A latch according to claim 1, wherein said hook portion is beveled adjacent its distal end.

6. A latch according to claim 1, wherein at least a portion of the top surface of said latch is serrated.

7. A latch according to claim 1, wherein said slot has a width which is significantly greater than the diameter of said rod.

8. A latch according to claim 1, wherein said rod is mounted in bosses formed on said lid.

9. A medical case for storage of medically-related instruments and equipment, said case comprising:
   a tray portion having an open top end, base and surrounding side walls;
   a lid sized and constructed to fit over said tray portion and close said open top; and
   at least one pair of slide action latches as claimed in claim 1, located opposite one another on said lid.

10. A medical case according to claim 9, and comprising two pairs of said slide action, latches.

\* \* \* \* \*